United States Patent [19]

Hall

[11] 4,047,523
[45] Sept. 13, 1977

[54] SURGICAL SACRAL ANCHOR IMPLANT

[75] Inventor: John Emmett Hall, Boston, Mass.

[73] Assignee: Downs Surgical Limited, Mitcham, England

[21] Appl. No.: 680,232

[22] Filed: Apr. 26, 1976

[30] Foreign Application Priority Data

Apr. 28, 1975  United Kingdom ............... 17610/75

[51] Int. Cl.² .............................................. A61F 5/00
[52] U.S. Cl. ....................................... 128/69; 128/78; 128/92 B
[58] Field of Search ................. 128/92 B, 92 R, 92 D, 128/92 E, 69, 78; 294/78 R; 56/400.17, 400.21, 400.1; 172/378, 380, 371

[56]  References Cited

U.S. PATENT DOCUMENTS

| 295,103 | 3/1884 | Booker | 56/400.17 |
| 855,159 | 5/1907 | Brown | 294/78 R |
| 1,706,658 | 3/1929 | Davis | 172/380 |
| 2,266,677 | 12/1941 | Ing | 172/378 |
| 3,605,123 | 9/1971 | Hahn | 3/1 |
| 3,824,995 | 7/1974 | Getscher et al. | 128/92 B |

FOREIGN PATENT DOCUMENTS 59,460  2/1924  Switzerland .......................... 172/380

Primary Examiner—Ronald L. Frinks
Attorney, Agent, or Firm—Haight & Huard

[57]  ABSTRACT

Surgical implant, known as a sacral anchor, for use in securing a cable to the sacrum in carrying out an operation for the correction of scoliosis.

14 Claims, 3 Drawing Figures

SURGICAL SACRAL ANCHOR IMPLANT

The invention relates to a surgical implant for use in the correction of curvature of the spinal column.

One technique that is used for the correction of spinal curvatures is the Dwyer technique of anterior instrumentation of the spine; (cf. A. F. Dwyer, "Anterior approach to scoliosis", *Journal of the Western Pacific Orthopaedic Association, Vol. VI*, No. 1, March 1969; A. F. Dwyer et al., "Anterior approach to scoliosis", *Clinical Orthopaedics and Related Research*, No. 62, pp. 192-202, 1969; and A. F. Dwyer, "Anterior approach to scoliosis", ibid, No. 93, July 1973). This technique involves operation on the front of the spine, with access to the spine being gained by the removal of one rib, or possibly of two ribs. This method may be used for the correction of scoliosis (lateral curvature of the spinal column) when posterior elements are absent, such as in myelomeningocele or after an extensive laminectomy. It is particularly useful when lordosis (curvature of the spinal column with a forward convexity) is associated with scoliosis, and can often be used as a supplementary means of fixation in a very long paralytic curves, especially those associated with lordosis in the lumbar region.

The technique involves the application of compression on the convex side of the spinal curve, after the contents of the discs have been excised, so as to straighten the curve. The compression is applied by means of a metal cable threaded through the heads of screws, one of which is anchored through a metal staple in each vertebra.

A staple or "saddle" of such a size as to fit snugly over the vertebra is first selected and driven into place over the vertebra. A screw is then passed through a hole in the staple and into the vertebra until only the head of the screw protrudes above the staple. A metal cable is passed through a hole in the head of the screw. The procedure is repeated on successive vertebrae with a single cable being passed through all screw heads. Tension is applied to the cable, to obtain the necessary corrective force, by means of a special tensioner. The tension may be applied one stage at a time, after the cable has been passed through each respective screw-head, or it may be applied after the cable has been passed through several or all of the screw-heads. When the correct tension has been obtained, the screw-head is crimped over the cable so as to maintain the cable at the necessary tension.

In carrying out this technique, one normally works from the top part of the spine to be corrected downwards, as this generally enables the final correction to be made at the most accessible level of spine, namely in the region of the lumbar vertebrae. If one were to work from the lumbar vertebrae upward to the thoracic vertebrae, instrumentation would be very difficult —the top screws would be difficult to apply and the tensioner would be awkward to use. When working from the top downward, however, difficulty occurs if instrumentation has to be continued down to the lumbo-sacral level, as is usually necessary when dealing with a paralytic curve or a curve associated with myelomeningocele. In these lower regions of the spine, it again becomes extremely awkward to use the tensioner, and, moreover, the screws and staples cannot conveniently be used on the sacral vertebrae.

The present invention provides a surgical implant for securing a cable to the sacrum, which comprises two laminar and substantially coplanar prongs rigidly secured together at their bases by a bridge portion which extends away from the prongs in a direction that makes an angle of not more than 90° with the plane of the prongs and on the side on which the prongs lie, and means for securing to the implant a cable extending substantially in the said direction in which the bridge portion extends.

This implant is used to fix the lower end of the metal cable to the sacrum, and it may be referred to as a sacral anchor. It is generally inserted with the bridge portion over the body of a sacral vertebra S1 and with the two prongs extending into the disc space S1/S2. Instrumentation is then carried out beginning at this level and continuing upward to the lumbar vertebrae.

Because of the previously mentioned difficulties encountered in continuing instrumentation upward to the thoracic vertebrae, it is advantageous, when working at the lumbo-sacral level, to use two cables. One of these is fixed first at the top and then worked downward to the lumbar region, generally to lumbar vertebra L3, and the other is fixed first at the bottom by means of the said anchor and worked upward to the lumbar region, generally to lumbar vertebra L2. The two cables overlap on these two vertebrae, and can both be secured by using two screws in each of these two vertebrae in conjunction with a further surgical implant, which may be referred to as a double-hole spinal staple, and which is described and claimed in the complete specification accompanying U.K. Patent Application No. 17611/75. The final tension can then be applied, and thus the final correction obtained, at this, the most accessible, level of the spine.

The anchor is of generally L-shaped profile, with the angle formed between the plane of the prongs and the direction in which the bridge extends being the included angle of the L-shape. This included angle must not be more than 90°, since if it were substantially more than 90°, the anchor would not hold in place sufficiently firmly; advantageously, the included angle is from 65° to 75°. Preferably, the included angle is substantially 70°, since this gives a combination of little danger of the anchor becoming dislodged (especially once tension has been applied to the cable passed through the receiving means) and little protrusion of the implant.

The end of each prong remote from the bridge is advantageously pointed, bevelled, and in a plane that makes an angle with the direction in which the bridge portion extends that is smaller than the aforementioned angle. These features assist in insertion of the sacral anchor and in reducing any risk of dislodgement of the anchor. The two prongs also advantageously converge slightly, away from the bridge and are sized and shaped for insertion into a spinal disc space. A suitable size for each prong is from 15 to 20 mm long by 5 to 7 mm wide, preferably substantially 18 mm long by substantially 6 mm wide. The distance between the two inner edges of the prongs is suitably about 11 mm at the end attached to the bridge and substantially 8 mm at the end remote from the bridge. The prongs are advantageously substantially 1 mm in thickness.

The means for receiving the metal cable may be a substantially cylindrical collet with its longitudinal axis cutting the plane in which the prongs lie at substantially the same angle as does the plane in which the bridge lies. A suitable length for the cylindrical collet is from 6 to 10 mm, preferably substantially 8 mm, and a suitable internal diameter is from 3 to 4 mm.

The prongs, bridge and collet are advantageously integral with one another, and the implant can be manufactured by stamping a suitable shape from a sheet of metal and bending it to the desired shape, the collet being formed simply by bending two flanges around to meet each other. The implant is advantageously made of titanium as this metal neither adversely affects, nor is adversely affected by, the body tissues.

One form of sacral anchor according to the invention will now be described, by way of example only, with reference to the accompanying drawings, in which.

Figure 1:
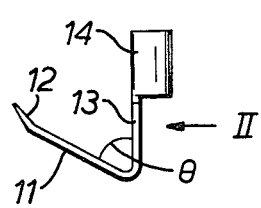
FIG. 1 is a side view of the sacral anchor.
Figure 2:
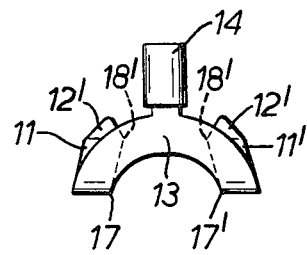
FIG. 2 is a view in the direction indicated by the arrow II shown in FIG. 1.
Figure 3:
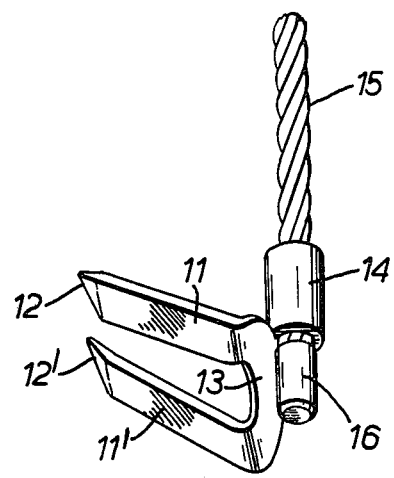
FIG. 3 is a perspective view of the sacral anchor with a cable passing through the cylindrical collet.

The sacral anchor is of substantially L-shaped profile, as can clearly be seen in FIG. 1. In one plane lie two laminar prongs 11, 11', which curve slightly upward, are bevelled and are pointed at the ends 12, 12' respectively. The two prongs are joined by a laminar bridge portion 13 formed integrally with the prongs, and a cylindrical collet 14 is formed integrally with the bridge portion 13. The bridge portion and the collet lie in a second plane, which meets the first-mentioned plane at an angle $\theta$ of about 70°. The collet 14 can receive a metal cable 15 (which will generally be a titanium cable), and this cable 15 will generally have a cylindrical collar 16 crimped to its end to secure the lower end of the cable 15 when upward tension is applied to the cable 15.

The sacral anchor is made from titanium about 1 mm thick. The prongs 11, 11' are each about 18 mm long by about 6 mm wide. The distance between the inner edges of the two prongs 11, 11' is about 11 mm at their widest separation, between the points 17, 17', and about 8 mm at between the points 18, 18'. The collet 14 is about 8 mm long and has an internal diameter of 3 to 4 mm.

In use, the sacral anchor is put in position with the two prongs 11, 11' in the disc space between two sacral vertebrae, generally in the disc space S1/S2, and with the bridge portion 13 over the body of the upper of the two sacral vertebrae, which will generally be sacral vertebra S1. A metal cable 15 is threaded through the collet 14, and the collar 16 prevents it from slipping right through the collet 14. Instrumentation is then continued upward by fixing screws and staples to the lumbar vertebrae in the usual manner, threading the cable 15 through these screws, and applying tension.

A special screw and nut for use in securing the metal staples to the vertebrae is described and claimed in the complete specification accompanying U.K. Patent Application No. 17612/75, and a special tensioner for applying the desired tension to the metal cable is described and claimed in the complete specification accompanying U.K. Patent Application No. 17613/75.

What I claim is:

1. In a surgical implant capable of securing a spinal tensioning cable to the sacrum, the improvement wherein said implant comprises two laminar and substantially coplanar prongs which are sized and shaped for insertion into a spinal disc space and are rigidly secured together at their bases by a bridge portion which extends away from the prongs in a direction that makes an angle of not more than 90° with the plane of the prongs and on the side on which the prongs lie, and means for securing to the bridge portion a spinal tensioning cable extending substantially in the said direction in which the bridge portion extends.

2. An implant as claimed in claim 1, wherein said angle is from 65° to 75°.

3. An implant as claimed in claim 2, wherein said angle is substantially 70°.

4. An implant as claimed in claim 1, wherein the end of each prong remote from the bridge is pointed, bevelled, and in a plane that makes an angle with the direction in which the bridge portion extends that is smaller than the aforementioned angle.

5. An implant as claimed in claim 1, wherein the two prongs converge slightly, away from the bridge.

6. An implant as claimed in claim 1, wherein each prong is from 15 to 20 mm long by 5 to 7 mm wide.

7. An implant as claimed in claim 6, wherein each prong is substantially 18 mm long by substantially 6 mm wide.

8. An implant as claimed in claim 7, wherein each prong is substantially 1 mm in thickness.

9. An implant as claimed in claim 1, wherein the means for securing the cable comprises a substantially cylindrical collet with its longitudinal axis intersecting the plane in which the prongs lie at substantially the same angle as does the plane in which the bridge lies.

10. An implant as claimed in claim 9, wherein the collet has a length of from 6 to 10 mm and an internal diameter of from 3 to 4 mm.

11. An implant as claimed in claim 9, wherein the prongs, bridge and collet are integral with one another.

12. An implant as claimed in claim 1, which is made of titanium.

13. An implant as claimed in claim 4, wherein the said angle is from 65° to 75°.

14. An implant as claimed in claim 13, wherein the means for securing the cable comprises a substantially cylindrical collet with its longitudinal axis intersecting the plane in which the prongs lie at substantially the same angle as does the plane in which the bridge lies.

* * * * *

UNITED STATES PATENT AND TRADEMARK OFFICE
CERTIFICATE OF CORRECTION

PATENT NO. : 4,047,523

DATED : September 13, 1977

INVENTOR(S) : John Emmett Hall

It is certified that error appears in the above-identified patent and that said Letters Patent are hereby corrected as shown below:

In the list of references cited under "Foreign Patent Documents", "Switzerland" should be ---Sweden---.

Signed and Sealed this

Fifteenth Day of May 1979

[SEAL]

Attest:

RUTH C. MASON
Attesting Officer

DONALD W. BANNER
Commissioner of Patents and Trademarks